United States Patent [19]

Cocks et al.

[11] Patent Number: 4,892,089

[45] Date of Patent: Jan. 9, 1990

[54] METHOD FOR COMMINUTING KIDNEY STONES

[75] Inventors: Franklin H. Cocks; Scott R. Akers, both of Durham, N.C.

[73] Assignee: Duke University, Durham, N.C.

[21] Appl. No.: 315,412

[22] Filed: Feb. 23, 1989

[51] Int. Cl.$^4$ .............................................. A61B 17/22
[52] U.S. Cl. .................................... 128/24 A; 604/22; 604/49
[58] Field of Search ............... 128/24 A, 328; 604/22, 604/28, 49

[56] References Cited

PUBLICATIONS

Johrde et al., Fracture Strength Studies of Renal Calculi Journal of Materials Science Letters 4 (1985), pp. 1264 & 1265.

Johrde et al., Microhardness Studies of Renal Calculi Materials Letters, vol. 3, No. 3, Jan. 1985, pp. 111, 112, 113 & 114.

Suby et al., Properties of Organic Acid Solutions which Determine their Irritability to the Bladder Mucuous Membrane and the Effect of Magnesium Ions in Overcoming this Irritability, pp.549 & 550.

Abbeshouse et al., Experimental Study of Solvent Action of Versene on Urinary Calculi, The Journal of Urology, vol. 65, No. 2, Feb. 1951, pp. 316 & 317.

Akers et al., Extracorporeal Shock Wave Lithotripsy: The Use of Chemical Treatments for Improved Stone Comminution, Journal of Urology 138 (1987), pp. 1295-1300.

*Primary Examiner*—Ruth S. Smith
*Attorney, Agent, or Firm*—Richard E. Jenkins

[57] ABSTRACT

A method for comminuting kidney stones including treating a stone to be comminuted with a renal matrix-attacking substance and applying acoustic impulses to the stone so as to pulverize the stone into fragments small enough to be passed through the ureter and urethra.

12 Claims, No Drawings

METHOD FOR COMMINUTING KIDNEY STONES

TECHNICAL FIELD

This invention relates generally to a method for comminuting kidney stones utilizing acoustic impulses, and more specifically to a treatment method which enhances the pulverizing effect of extracorporeal shock wave lithotripsy.

BACKGROUND ART

Kidney stones, also known as renal calculi, develop within the kidney and are in many cases too large to pass through the ureter and urethra. The stones are composed of both organic and inorganic materials. The inorganic components comprise most of the mass of the stone and are typically rigid crystalline masses of calcium or magnesium oxalates, phosphates, or various urates. The inorganic components ar different for each particular type of stone and therefore each stone may have different characteristics depending on the composition of its inorganic component.

The organic component of the stone is called the organic matrix (or renal matrix) and often forms an intricate mesh from the surface of the stone to the center of the stone. Although the organic component often comprises a small percentage (approximately 3% to 6%) of the entire kidney stone, it forms a mesh that extends throughout the stone and can be viewed as a "backbone" of the stone. The matrix composition is essentially the same in each urinary stone and typically comprises about 64% protein, 9.6% non-amino sugar, 5% glucosamine, and 10% bond water. The remainder of the matrix composition is inorganic ash composed mainly of calcium and various phosphates.

Kidney stones must either be surgically removed or somehow reduced to fragments small enough to comfortably pass through the ureter and urethra. Various techniques have been developed in an attempt to provide a safe and effective method of eliminating kidney stones from the human body and thereby to avoid surgical removal of the stones. One such technique involves the dissolution of urinary calculi by organic or inorganic acid solutions or reagents. This technique suffers from the fact that the acid solutions or reagents can be very irritating to the patient undergoing treatment and the time frame for dissolution is often excessively long.

Presently, several non-invasive sonic methods, invasive ultrasonic methods and laser fragmentation methods to destroy kidney stones are being explored. For example, extracorporeal shock wave lithotripsy (ESWL) is of considerable current interest and involves applying focused intense acoustic impulses which produce pressure waves greater than one kbar in amplitude. These acoustic impulses are repeatedly applied to the stone until the stone is pulverized or comminuted into fragments small enough to be passed through the ureter and urethra. Unfortunately, the acoustic pulses cannot be precisely focused onto the stone and therefore portions of the healthy kidney normally receive some of the concentrated shock waves. Since the pulses often are applied up to 2000 times in a single treatment to pulverize a stone, the healthy portions of the kidney receiving the shock waves can be injured, resulting in hematuria. Furthermore, the shock-producing electrodes utilized in ESWL are expensive and have a limited useful life. Since ESWL requires extensive repetition of acoustic impulses, the electrodes frequently become exhausted and require replacement which results in considerable lithotripter equipment expense and inconvenience.

In applicant's previous U.S. patent application Ser. No. 132,413, filed Dec. 14, 1987 and now U.S. Pat. No. 4,825,851, an alternative method for comminuting kidney stones is described which comprises introducing a surface energy lowering solution into a kidney such that a stone within the kidney is exposed to the solution and the surface energy lowering solution weakens the inorganic component of the stone to be comminuted so that the stone is more easily pulverized by acoustic impulses. This method requires a specific and different surface energy lowering solution for each stone to be comminuted depending on the content of the inorganic component of the stone.

A need therefore exists for a single method of acoustically comminuting all types of kidney stones which utilizes a reduced number of acoustic impulses so as to minimize trauma to healthy tissue and reduce exhaustion of shock-producing electrodes in ESWL equipment. The technique disclosed hereinafter should overcome the deficiencies associated with current renal calculi comminution techniques.

DISCLOSURE OF THE INVENTION

The kidney stone comminuting method of the present invention involves exposing a stone to be treated to a renal matrix-attacking substance which thereby lowers the fracture strength of the stone and then subjecting the stone to acoustic impulses so that the stone is pulverized into fragments which will safely pass through the ureter and urethra. The present invention takes advantage of the fact that the organic matrix or backbone is essentially the same for all types of stones and utilizes renal matrix-attacking substances which affect the organic matrix of all types of kidney stones regardless of the composition of the inorganic components of the stones.

The renal matrix-attacking substances may be introduced into the kidney by means of catheters normally used during lithotripter treatment. The method of the present invention can be applied to any type of stone regardless of the composition of the inorganic component of the stone. The lower fracture strength or hardness of the stone allows for fewer repetitions of uses being required to sufficiently comminute the stone. The reduction in repetitions of pulses results in less damage to healthy kidney tissue and less exhaustion or depletion of the impulse-producing electrodes of ESWL equipment.

It is therefore a principal object of the present invention to provide a method of acoustically comminuting renal calculi which minimizes damage to healthy portions of a kidney.

It is another object of the present invention to provide a single method of acoustically comminuting kidney stones which will be applicable to all types of kidney stones regardless of the composition of the inorganic components of the stones.

It is a further object of the present invention to provide a method of acoustically pulverizing kidney stones which will avoid rapid exhaustion of the impulse-producing electrodes utilized by ESWL equipment.

It is still a further object of the present invention to provide a method of acoustically comminuting kidney stones which requires minimal repetition of impulses in order to fully pulverize the stone into fragments small enough to comfortably pass through the ureter and urethra.

BEST MODE FOR CARRYING OUT THE INVENTION

The method of the present invention involves treating a stone to be comminuted with a renal matrix-attacking substance and then applying acoustic impulses to the stone in order to pulverize it into fragments small enough to pass through the ureter and urethra. The present method may be carried out during normal lithotripter treatment and may utilize catheters typically associated with lithotripter treatment. The renal matrix-attacking substance is preferably passed through a catheter into the kidney so as to come into contact with the stone to be pulverized although it is contemplated that the renal matrix-attacking substance may also be transmitted to the kidney in any other suitable manner such as by oral, parenteral, sublingual or buccal administration. The renal matrix-attacking substance would normally be transmitted to the kidney prior to the application of the acoustic shocks, and the length of exposure time before shock treatment can range from about 5 minutes to about 10 hours. Normally, the stones would also be exposed to the renal matrix attacking substance during the actual pulverization treatment by the lithotripter machine. Although standard clinical usage requires application of 2,000 acoustic pulses to a stone, applicant's invention should result in a reduction of at least one-half in the number of required pulses to comminute a stone and may require application of no more than 200 acoustic impulses.

Any lithotripter machine which produces acoustic shocks of sufficient strength to comminute kidney stones can be utilized in practicing the method of the present invention. However, the preferred apparatus used in conjunction with the present method is a DORNIER lithotripter operated under typical clinical voltage conditions ranging from 18 kV to 21 kV.

The renal matrix-attacking substance contemplated by the present invention can be any substance which will affect or weaken the penal matrix material of any type of stone so as to decrease the fracture strength of the stone and thus render the stone more susceptible to the pulverizing effect of acoustic impulses. The renal matrix-attacking substance should be utilized in a form that is non-irritating to the urinary passage of the epithelium, non-toxic, and easy to make and store.

Typical substances which affect the organic matrix of a kidney stone for purposes of the present invention include enzymes which attack and degrade the renal matrix and denaturing agents which act to "unfold" the protein in the renal matrix from its natural configuration. Typical enzymes would be from the hydrolases class and include proteases, proteinases, peptidases, glycosidases and other proteolytic enzymes. Typical denaturing agents include acids, alkali, alcohols, concentrated urea, and detergents. Other substances are also contemplated for use in the method of the present invention. It has specifically been found that the enzymes peptidase and protease are effective at pH 7 in attacking the renal matrix of kidney stones and lowering the overall fracture strength of the stones so as to render the stones more susceptible to the pulverizing effect of acoustic impulses during ESWL treatment.

The renal matrix-attacking substance is typically combined with a diluent or carrier depending on the particular method of administration and is preferably diluted with distilled water in order to form a solution which can readily be applied through a catheter to a kidney stone of a patient undergoing ESWL treatment.

Clinical Test Results

The effectiveness of the method of the present invention was tested under clinical conditions using a DORNIER lithotripter operated under typical clinical voltage conditions ranging from 18 kV to 21 kV. For the clinical testing, each stone was severed into two equal halves with one half being used for the control environment of synthetic urine at neutral pH 7 and with the other half being used for the altered environment consisting of a solution continuing either peptidase or protease. Table 1 indicates the components of the synthetic urine utilized in the testing. The peptidase used was produced from porcine intestinal mucosa and had general proteolytic and amniopeptidase activity. The solution concentration consisted of 44 mg of peptidase, with an activity of 115 units/mg, placed in 50 ml of distilled water. However, the solution could suitable comprise between about 30-50 mg of peptidase and about 40-60 ml of distalled water. The protease used was crystallized and lyophilized from bacillus licheniformis. The solution concentration consisted of 100 mg of protease, with an activity of 9.3 units/mg of solid, dissolved in 50 ml of distilled water. However, the solution could suitably comprise between about 90-110 mg of protease and about 40-60 ml of distilled water.

The calculi to be tested were contained in a flexible elastomeric fixture which contained both the stones and the environment to which the stones were subjected. This fixture was suspended in a water-filled lithotripter tub and positioned using the standard X-ray positioning technique for the DORNIER lithotripter. The control stones were exposed to the synthetic urine solution and the altered environment stones were exposed to the solutions containing the renal matrix-attacking substances for 8 hours prior to being subjected to 200 acoustic shocks, and exposure of the stones to the solutions was continued during the shocking process. The comminuted stone fragments were washed with distilled water to remove any salts remaining from the solution to which they had been exposed and weighed after sufficient desiccation over calcium sulphate.

The degree of comminution was quantitatively assessed by sequential sieving of the dried fragments using a series of U.S. standard sieves. The mesh dimensions of the series of sieves used is shown in Table 2. Finally, Table 3 displays the data obtained for calculi (kidney stones) consisting primarily of phosphates exposed to (1) synthetic urine of pH 7 and to (2) the solutions containing the renal matrix-attacking substances pepsin and protease. The tables described herein ar now set forth below as follows:

TABLE 1

Composition of Synthetic Urine

| Constituents | Molecular Formula | Synthetic Urine Concentration (gm./l.) |
|---|---|---|
| Urea | $H_2NCONH_2$ | 17.5 |
| Sodium Chloride | NaCl | 7.6 |
| Potassium Chloride | KCl | 3.4 |
| Creatinine | $C_4H_7N_3O$ | 1.0 |
| Glycine | $C_2H_5NO_2$ | 0.93 |
| Hippuric Acid | $HC_2H_6NO_3$ | 0.64 |
| Citric Acid | $C_6H_8O_7$ | 0.54 |
| Water | $H_2O$ | 1.0 liter |

TABLE 2

ASTM Standard Wire Cloth Sieve Dimensions

| Sieve No. | Nominal Sieve Opening | |
|---|---|---|
| | Inches | (mm) |
| No. 8 | 0.187 | (2.36) |
| No. 16 | 0.0469 | (1.18) |
| No. 30 | 0.0234 | (0.600) |
| No. 50 | 0.0117 | (0.300) |
| No. 100 | 0.0059 | (0.150) |
| No. 200 | 0.0029 | (0.075) |
| No. 400 | 0.0015 | (0.038) |

TABLE 3

Sieve Distributions for Phosphate Stones Comminuted in Protease and Peptidase Solutions and Neutral Synthetic Urine Solutions

| Test | Composition of Inorganic Comp. of Stone | Stone wt. (grams) | Time in solution (hrs.) | Type of solution | Sieve #: Stone Fraction Weight % Retained on Specified Sieves | | | | | | | |
|---|---|---|---|---|---|---|---|---|---|---|---|---|
| | | | | | 8 | 16 | 30 | 50 | 100 | 200 | 400 | 400 |
| 1 | CA/COM/MAPH | 0.5010 | 8 | Syn. 7 | 4.2 | 23.7 | 29.7 | 18.6 | 8.1 | 5.3 | 6.1 | 4.8 |
|   | CA/COM/MAPH | 0.5000 | 8 | Peptidase |     | 17.3 | 30.5 | 21.7 | 9.7 | 4.7 | 0.9 | 15.2 |
| 2 | MAPH/CA | 0.8238 | 8 | Syn. 7 | 15.8 | 20.5 | 14.2 | 14.1 | 12.5 | 10.2 | 4.2 | 8.5 |
|   | MAPH/CA | 0.8249 | 8 | Protease | 6.1 | 18.3 | 22.7 | 21.2 | 12.5 | 8.6 | 2.0 | 8.6 |

Note:
MAPH = Magnesium Ammonium Phosphate Hexahydrate
COM = Calcium Oxalate Monohydrate
CA = Carbonate Apatite
Peptidase = Peptidase (pH 7)
Protease = Protease (pH 7)
Syn. 7 = Synthetic urine of pH 7

The data in Table 3 illustrates that the degree of comminution experienced during extracorporeal shock wave lithotripsy can be significantly enhanced by the use of a renal matrix-attacking substance as contemplated by the method of the present invention. More specifically, it can be seen that the weight percentage of stone fraction retained by the largest sieves (Nos. 8 & 16) was reduced from 27.9% to 17.3% in Test 1 and was reduced from 36.3% to 24.4% in Test 2. This reduction in large fragment size is very significant since the largest stone fragments present the most difficulty during passage through the ureter and urethra and pose the greatest potential for pain and blockage of the urinary tract. The smaller fragments are of far less concern since they tend to pass through a patient's urinary tract and are consequently eliminated.

In summary, the use of a renal matrix-attacking substance reduces the number of acoustic impulses needed for any given degree of pulverization, and provides a concomitant reduction in the collateral damage to the kidney as well as an increase in the number of patients who can be treated before the impulse-producing electrodes must be replaced. The use of a renal matrix-attacking substance in accordance with the present invention can effectively lower the fracture strength of any type of stone regardless of the composition of the inorganic component of the stone.

The present invention is not limited by the foregoing description but is intended to encompass various modifications within the scope and spirit of the invention described above. The scope of the invention is appropriately defined by the following claims.

We claim:

1. A method for comminuting kidney stones with a lithotripter comprising:
   exposing a stone to be comminuted to a renal matrix-attacking substance, said substance being a substance other than acid; and
   applying acoustic impulses to said stone; whereby the renal matrix-attacking substance lowers the fracture strength of the stone to be comminuted so that the stone is more easily pulverized by the acoustic impulses.

2. A method according to claim 1 wherein the renal matrix-attacking substance is an enzyme.

3. A method according to claim 2 wherein the enzyme is peptidase.

4. A method according to claim 2 wherein the enzyme is protease.

5. A method according to claim 1 wherein the renal matrix-attacking substance is a denaturing agent.

6. A method according to claim 1 wherein the

7. A method for comminuting kidney stones with a lithotripter comprising:
   introducing a solution containing a renal matrix-attacking substance into a kidney such that a stone within the kidney is exposed to said solution, said substance being a substance other than acid; and
   applying focused intense acoustic impulses to the stone after introduction of said solution; whereby the stone is comminuted into fragments small enough to be passed through the ureter and urethra with minimized risk of damage to the kidney from said acoustic impulses.

8. A method according to claim 7 wherein the solution comprises from about 30 to about 50 mg of peptidase and from about 40 to about 60 ml of distilled water.

9. A method according to claim 7 wherein the solution comprises from about 90 to about 110 mg of protease and from about 40 to about 60 ml of distilled water.

10. A method according to claim 7 wherein the

11. A method according to claim 7 wherein the acoustic impulses are applied by a lithotripter operated from about 18 kV to about 21 kV.

12. A method according to claim 7 wherein at least about 200 focused intense acoustic impulses are applied to the stone after introduction of said solution.

* * * * *

UNITED STATES PATENT AND TRADEMARK OFFICE
CERTIFICATE OF CORRECTION

PATENT NO. : 4,892,089
DATED : January 9, 1990
INVENTOR(S) : Cocks et al.

It is certified that error appears in the above-identified patent and that said Letters Patent is hereby corrected as shown below:

Col. 1, line 3, after the title and before "Technical Field" please insert:

-- GOVERNMENT INTEREST

This invention was made with Government support under Grant #DK 36331 awarded by the National Institute of Health. The Government has certain rights in this invention. --

Signed and Sealed this

Fourth Day of April, 1995

*Attest:*

BRUCE LEHMAN

*Attesting Officer*     *Commissioner of Patents and Trademarks*